US008888790B2

(12) United States Patent
Grace et al.

(10) Patent No.: US 8,888,790 B2
(45) Date of Patent: Nov. 18, 2014

(54) DEVICE FOR THE REMOVAL OF UNSIGHTLY SKIN

(75) Inventors: Christopher R. Grace, Russellville, AR (US); Louis Paul Chalfant, Jr., Russellville, AR (US)

(73) Assignee: Telebrands Corp., Fairfield, NJ (US)

( * ) Notice: Subject to any disclaimer, the term of this patent is extended or adjusted under 35 U.S.C. 154(b) by 864 days.

(21) Appl. No.: 11/720,948

(22) PCT Filed: Dec. 21, 2004

(86) PCT No.: PCT/US2004/042845
§ 371 (c)(1),
(2), (4) Date: Oct. 4, 2007

(87) PCT Pub. No.: WO2006/068638
PCT Pub. Date: Jun. 29, 2006

(65) Prior Publication Data
US 2008/0091216 A1    Apr. 17, 2008

(51) Int. Cl.
| A61B 17/50 | (2006.01) |
| A61B 17/54 | (2006.01) |
| A61B 17/322 | (2006.01) |
| A61B 17/00 | (2006.01) |
| A61B 17/32 | (2006.01) |

(52) U.S. Cl.
CPC .............. *A61B 17/54* (2013.01); *A61B 17/322* (2013.01); *A61B 2017/00761* (2013.01); *A61B 2017/320008* (2013.01)
USPC ........................................ 606/131

(58) Field of Classification Search
USPC ......... 606/131, 167; 132/76.4, 76.5; 451/538, 451/539, 552, 557, 558
See application file for complete search history.

(56) References Cited

U.S. PATENT DOCUMENTS

| 107,808 | A | 9/1870 | Phillips |
| 297,816 | A | 4/1884 | Ledward |
| 788,236 | A | 4/1905 | Bartholomew |
| 852,873 | A | 5/1907 | Davidson |
| 1,498,156 | A | 6/1924 | Drew |
| 1,714,371 | A | 11/1929 | Jackson |
| 2,573,487 | A | 10/1951 | Potvin |
| D167,270 | S | 7/1952 | Marcus |

(Continued)

FOREIGN PATENT DOCUMENTS

| DE | 3320594 | 12/1984 |
| DE | 19624578 | 1/1998 |

(Continued)

OTHER PUBLICATIONS

Broussard, M., Foot for Thought, Apr. 17-23, 2003, archives. citypaper.net/articles/2003-04-17/cover5.shtml.*

(Continued)

*Primary Examiner* — Ashley Fishback
(74) *Attorney, Agent, or Firm* — Cooper & Dunham LLP

(57) ABSTRACT

A device for the removal of unwanted excess skin from an area of the human body to be treated in which a carrier encases a planing blade. The blade body is formed from a blank and co planer uniform opposed cutting edges protrude upwardly in a uniform transition beyond the plane of the blank in order to contact the skin to be removed while the device is moved to and fro across the area of the skin to be treated.

16 Claims, 2 Drawing Sheets

(56) References Cited

U.S. PATENT DOCUMENTS

| | | |
|---|---|---|
| 2,612,683 A | 10/1952 | Potvin |
| 2,714,908 A | 8/1955 | Carmack |
| 2,746,461 A | 5/1956 | Bocchino |
| D186,752 S * | 11/1959 | Dean .............................. D28/59 |
| 3,036,962 A | 5/1962 | McNutt |
| 3,045,321 A | 7/1962 | McDermott |
| 3,079,669 A | 3/1963 | Bryant |
| 3,279,043 A | 10/1966 | Wirt |
| 3,600,803 A | 8/1971 | Nachsi |
| 3,619,878 A | 11/1971 | Benis et al. |
| 3,636,625 A | 1/1972 | Pracht |
| 3,738,879 A | 6/1973 | Von Siemens |
| 3,762,243 A | 10/1973 | Borrkfield |
| 3,797,505 A | 3/1974 | Gilhaus et al. |
| 3,905,080 A | 9/1975 | Bond |
| 4,037,793 A * | 7/1977 | Puustinen ....................... 241/30 |
| 4,057,053 A | 11/1977 | Kunz |
| 4,075,919 A | 2/1978 | Komura et al. |
| 4,099,935 A | 7/1978 | Bond et al. |
| 4,124,437 A | 11/1978 | Bond et al. |
| 4,126,510 A | 11/1978 | Moscony et al. |
| D251,103 S | 2/1979 | Puustinen |
| 4,240,806 A * | 12/1980 | Frantzen ......................... 51/295 |
| 4,256,156 A | 3/1981 | Biszantz et al. |
| 4,283,820 A | 8/1981 | Willinger |
| 4,411,597 A * | 10/1983 | Koffel et al. ..................... 416/92 |
| 4,422,465 A * | 12/1983 | Haga ............................. 132/76.4 |
| D276,812 S | 12/1984 | Kanazawa |
| 4,497,686 A | 2/1985 | Weglin |
| 4,537,207 A | 8/1985 | Gilhaus |
| D294,071 S | 2/1988 | Lallerstedt |
| 4,790,488 A * | 12/1988 | Borner ............................. 241/95 |
| 4,793,218 A | 12/1988 | Jordan et al. |
| 5,082,009 A | 1/1992 | Cromer |
| 5,083,734 A * | 1/1992 | Ancona et al. ................. 248/687 |
| 5,100,506 A * | 3/1992 | Sturtevant et al. ............... 216/47 |
| 5,302,234 A | 4/1994 | Grace et al. |
| D364,226 S | 11/1995 | Hartmann |
| 5,522,136 A | 6/1996 | Larisey |
| 5,564,189 A | 10/1996 | Lee |
| 5,570,700 A | 11/1996 | Vogeler |
| 5,653,024 A | 8/1997 | Cartagenova |
| 5,711,491 A * | 1/1998 | Molo .............................. 241/95 |
| D393,986 S * | 5/1998 | Joergensen .................... D7/678 |
| 5,832,610 A | 11/1998 | Chaplick |
| 5,881,735 A | 3/1999 | Kutnik |
| 5,913,313 A | 6/1999 | Brunderman |
| D431,096 S | 9/2000 | Rieser |
| 6,142,156 A | 11/2000 | Brunderman |
| D442,741 S | 5/2001 | Rieser |
| 6,283,978 B1 | 9/2001 | Cheski et al. |
| D460,186 S | 7/2002 | Park |
| D460,554 S | 7/2002 | Park |
| 6,481,443 B1 | 11/2002 | Moore-Johnson et al. |
| D483,910 S | 12/2003 | O'Brien, II |
| D486,268 S | 2/2004 | Chien |
| 6,733,595 B1 | 5/2004 | Grillo |
| D491,774 S | 6/2004 | Brousseau et al. |
| D494,026 S | 8/2004 | Brousseau et al. |
| D496,731 S | 9/2004 | Park |
| D499,313 S | 12/2004 | Lawson et al. |
| 7,093,603 B2 | 8/2006 | Han |
| 2002/0087167 A1 | 7/2002 | Winitsky |
| 2005/0061343 A1 | 3/2005 | Ebner |

FOREIGN PATENT DOCUMENTS

| | | |
|---|---|---|
| GB | 783479 | 9/1957 |
| GB | 845832 | 8/1960 |
| JP | 56052127 | 5/1981 |
| JP | 56112475 | 9/1981 |
| JP | 56112476 | 9/1981 |
| JP | 561563270 | 12/1981 |
| KR | 20030096747 | 12/2003 |
| WO | WO 03024290 | 3/2003 |
| WO | WO2004/075764 | 9/2004 |

OTHER PUBLICATIONS

DishMan and TamedBill, "How to remove dead skin?", Oct. 12, 2004, www.pprune.org/archive/index.php/t-148122.html, p. 1.*
English language abstract of German Patent Publication No. DE 19624578, esp@cenet database, Jan. 8, 1998.
English language abstract of West German Patent Application No. De 3320594, esp@cenet database, Dec. 13, 1984.
English language abstract of Republic of Korea Patent Publication No. KR 20030096747, esp@cenet database, Dec. 31, 2003.
English language abstract of Japan Patent Publication No. JP 56052127, esp@cenet database, May 11, 1981.
English language abstract of Japan Patent Publication No. JP 56112475, esp@cenet database, Sep. 4, 1981.
English language abstract of Japan Patent Publication No. JP 56112476, esp@cenet database, Sep. 4, 1981.
English language abstract of Japan Patent Publication No. JP 56163270, esp@cenet database, Dec. 15, 1981.
"Nutmeg Grater", 4 pages, <http://www.silvercollection.it>, before 2007.
English language translation of Japan Patent Publication No. JP 56052127, May 11, 1981.
English language translation of Japan Patent Publication No. JP 56112475, Sep. 4, 1981.
Kauffmann, Stephane, "Intellimouse Wireless Explorer",Oct. 26, 2001, Tom's Hardware Guide.
"CVS Pumice Stone" and package, 1 page.
"Neat Feet Trim Pumice Stone" and package, 1 page.
"Parmenide design Alejandro Ruiz" and package, 2 pages.
"Cheese Grater by Bodum.com" and package, 2 pages.
"Cheese Grater Parmesanreibe—Thomas Rosenthal Group" and package, 2 pages.
"Pedicure Tool by Avon Products Inc.", 2 pages.

* cited by examiner

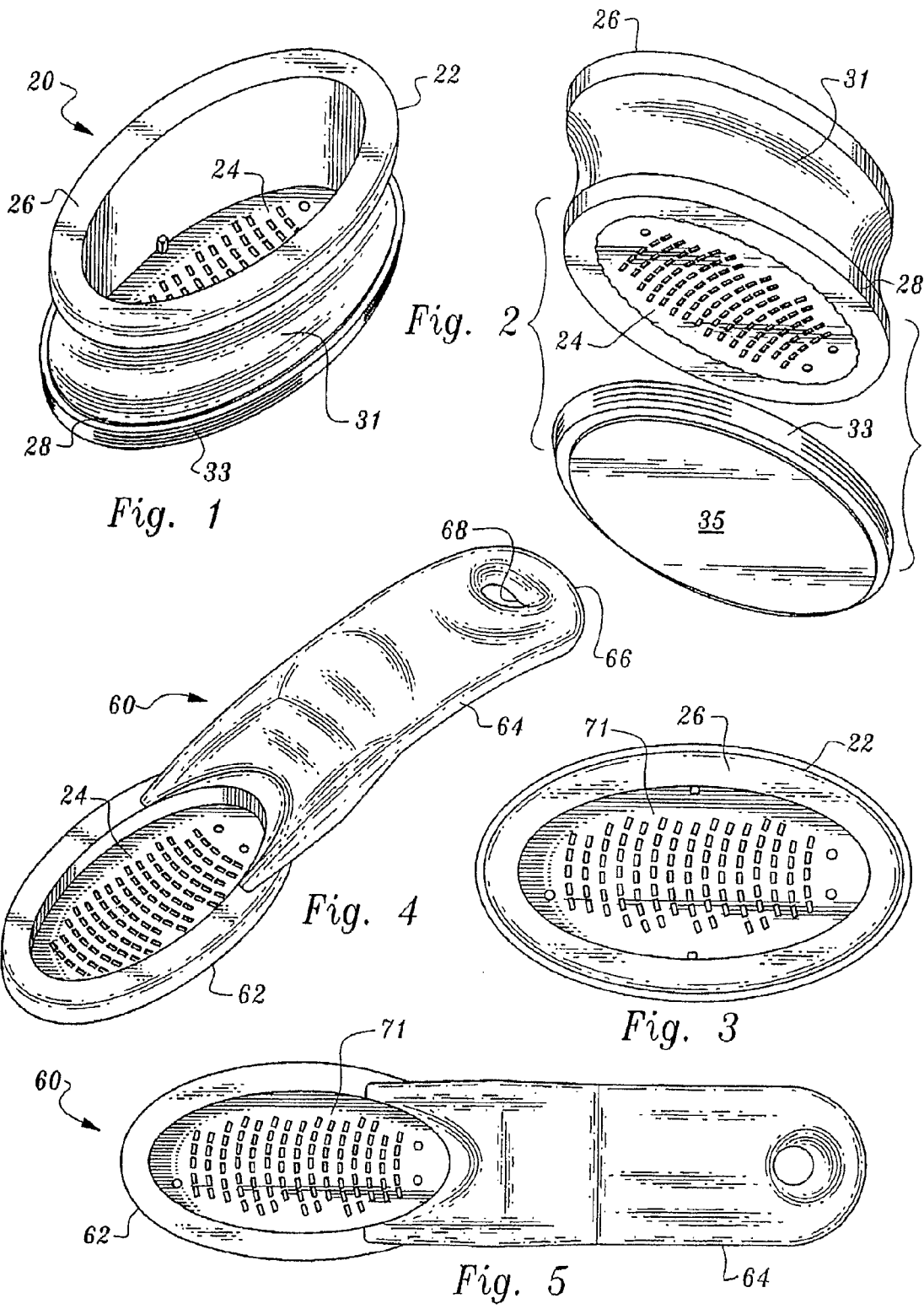

DEVICE FOR THE REMOVAL OF UNSIGHTLY SKIN

The present invention relates generally to devices for removal of dead skin, callouses and other unsightly buildup of excess skin on the feet, elbows and other areas of the human body and, more particularly, to a manually operated device which painlessly removes such unsightly skin without damaging or unnecessarily abrading good skin.

CROSS-REFERENCE TO RELATED APPLICATIONS

Not applicable.

STATEMENT REGARDING FEDERALLY SPONSORED RESEARCH OR DEVELOPMENT

Not applicable

INCORPORATION-BY-REFERENCE OF MATERIAL SUBMITTED ON A COMPACT DISC

Not applicable.

REFERENCE TO A "MICROFICHE APPENDIX"

Not applicable.

BACKGROUND OF THE INVENTION

1. Field of the Invention

A callous is typically a buildup of a thickened outer layer of skin. Corns have an inner core which penetrates the epidermis. Both tend to develop from some irritant, and, while callouses are typically not painful, corns may well be painful and both conditions are unsightly and often uncomfortable.

Concern for corns, callouses and other skin buildups dates back to at least 2400 B.C., as evidenced by reliefs and other evidence found at, and in, the Tomb of the Physician in ancient Egypt. Hippocrates expressed the need for care of such problems in pre biblical times in Greece.

Today, skin care generally, and the removal of corns, callouses, and other unsightly skin buildups, has become a billion dollar business, according to the American Academy of Dermatology.

The number and type of products for removal of dead skin is voluminous, ranging from abrasives such as sandpaper, rasps and emery boards, which simply abrade the skin, to blade type devices such as razors, knives and scrapers, which are prominent in the art, and which actually cut away unwanted skin, to pierced metal devices.

In the pierced metal devices, holes are punched into a metal sheet, causing a series of raised, essentially conical, bumps, in which the continuous edge about the opening is the result of the tearing of the metal by the punch, but because of its macroscopic size, serves to remove unwanted skin by abrading or scraping it off.

There are also myriad, often perfumed, chemicals available to consumers, which chemically soften and dissolve such buildups of unwanted and unsightly skin.

All of these products, whether used for cosmetic or medical purposes, are susceptible to excesses which can result in damage to viable growing tissue.

2. Description of Related Art

At least some of the various forms of devices for the removal of unwanted skin have been patented, although many simply come to the market in neat and attractive packaging. One of the earlier patents related to the use of a blade for the trimming and removal of corns and callouses was issued to Jackson as U.S. Pat. No. 1,714,371. Jackson's device resembles the venerable safety razor and professes to eliminate deep cuts.

Several other blade type devices have achieved patent status, among them Potvin U.S. Pat. No. 2,612,683 in which the head is formed with a recess, which receives a flat blade used to trim away excess dead skin. Potvin also issued U.S. Pat. No. 2,573,487 in which the blade is recessed behind a head 4.

Other blade type callous removers include Pracht U.S. Pat. No. 3,636,625, and Gilhaus et. al U.S. Pat. No. 3,797,505.

The art is replete with sand papers and emery boards, all in common usage. Many are encased in an attractive and decorative handle, primarily for sales purposes. Others are powered, whether by battery or other electrical means.

At least one such file has been patented as a nail file, i.e., Haga U.S. Pat. No. 4,422,465. While not specifically designed as a device for removing excess skin, it nonetheless seemingly has that capacity, and it is formed by a photochemical etching process, although the process differs in significant ways from that employed by the present invention.

BRIEF SUMMARY OF THE INVENTION

Notwithstanding the expansive variety of manually manipulated products for the removal of unsightly accumulation of skin in the form of callouses, corns, and the like, the consumer continues to seek out a product which is affordable, yet very safe in its use, and easily cleaned and stored until next used. Such is the micro slicing product of the present invention.

Coincident with the foregoing, it is an objective of the present invention to provide the consumer with a skin care product which is trustworthy and very simple to use, while providing significantly improved skin removal.

It is another objective of the present invention to provide a skin care device which channels away, removed epidermal remnants, dirt and bacteria that have been excised from an area of the body being treated, so that there will be no clogging or impairment of the ability of the cutting edge to achieve full contact with the area to be treated and, further, will not deposit grit, or the like, while providing exceptional cleaning characteristics.

It is a further objective of the present invention to provide a manually manipulable device for the removal of unsightly skin buildup, the cutting surface of which is formed, at least in part, by a photochemical etching process, as distinguished, e.g., from a metal piercing process, to provide a sharper, more durable, cutting or planing surface, which leaves the surface being treated relatively smooth, rather than the roughened surface to be expected from use of existing files or emery boards and, generally, by metal piercing methods of formation.

It is yet another, and still further, objective of the present invention to provide a device as described which is capable of at least bi_directional, and in other embodiments, multi-directional, operation.

The foregoing objects and advantages of the present invention, in addition to others not specifically articulated, will occur to those skilled in the art when the following Detailed Description of a Preferred Embodiment is read in conjunction with the accompanying drawings, wherein:

BRIEF DESCRIPTION OF THE SEVERAL VIEWS OF THE DRAWINGS

FIG. 1 is a perspective view of one embodiment of the present invention illustrating a palm controlled carrier device as viewed from above;

FIG. 2 is an additional perspective view of the embodiment of FIG. 1, as viewed from beneath the device, and further illustrating a cap which protects the cutting edges of the device from dirt, lint and the like when not in use;

FIG. 3 is a top plan view of the palm held device of FIG. 1, illustrating a pattern of cutting teeth formed on a blade body secured in the carrier of FIG. 1;

FIG. 4 is a view, in perspective, of a carrier device which shows the blade body in place, and includes an elongated handle;

FIG. 5 is a top plan view of the carrier device of FIG. 4;

DETAILED DESCRIPTION OF THE INVENTION

Figure 9:
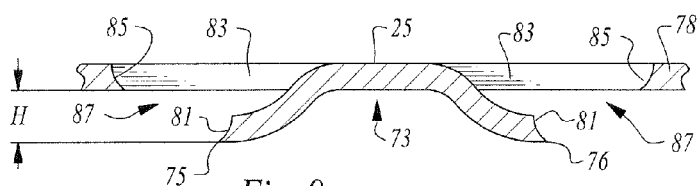
FIG. 9 is a side elevation of the tooth configuration of the plane cutter of FIG. 8 taken along lines 9-9 of FIG. 8.
Figure 10:
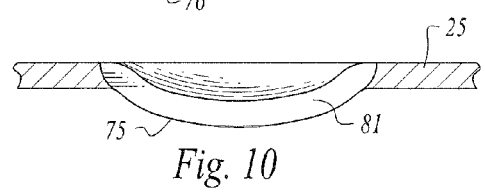
FIG. 10 illustrates an alternative to the structure.
Figure 11:
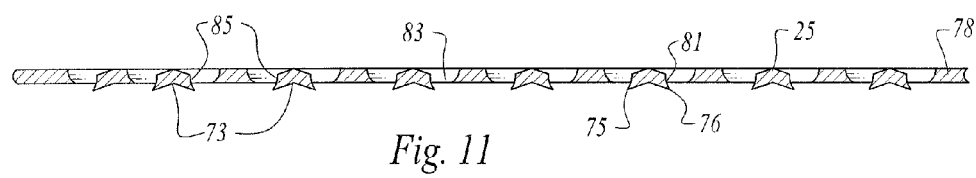
FIG. 11 is a partial sectional view of the plane body taken along lines 11-11 of FIG. 6.

With reference now to the drawings, and initially to FIGS. 1 and 9, a blade type device for the manual removal of unwanted and unsightly skin, constructed in accordance with the present invention, is depicted at 20. The device 20 comprises a carrier 22 which supports a blade body 24.

In the FIG. 1 embodiment, the carrier 22 is adapted to be held in the palm of one's hand, such that the blade body faces away from the palm and is movable against and across the area to be treated while in that position.

The carrier, in its illustrated form, is of an upstanding shell having a generally oval shape as viewed in FIGS. 1 and 3, for example. It will be appreciated that some variation in the specific shape is within the contemplation of the invention so long as it conforms to the purposes attributable to it.

The shell has an upper ridge 26, and a lower ridge 28, with a center section 31. The center section has a generally concave side wall which enhances one's ability to grip the device. The carrier, for economy and simplicity's sake, is preferably made of a moldable material, such as any number of well known plastic materials, although it will become apparent that any number of formable materials, including wood and certain metals, could be effectively used.

In keeping with the safety aspects of the invention, and referring to FIG. 2, an auxiliary cap 33 may be provided. The cap 33 fits about and snaps into place about the lower ridge 28 of the carrier 22. The free surface 35 of the cap may have an abrasive coating thereon to serve as a buffer to smooth any skin which may have been roughened during the skin removal process.

In order to maximize the efficiency of the device while achieving optimum safety and smoothness as the dead skin is removed from the area to be treated, the blade body 24, includes a tooth configuration which provides, in accordance with the invention, a bi-directional planing action when moved to and fro across the user's unsightly build up of skin to be treated.

Figure 6:
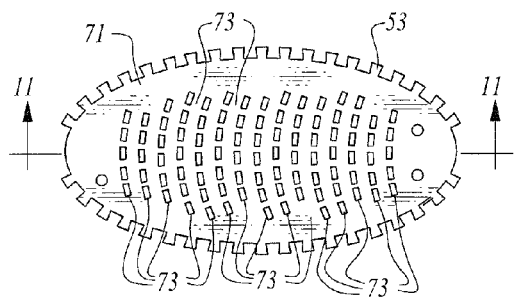
FIG. 6 is top plan view of a blade body constructed in accordance with the present invention.
Figure 7:
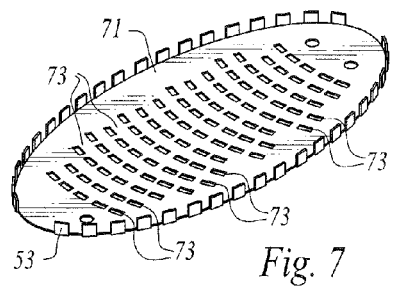
FIG. 7 is a perspective view of the blade body of FIG. 6 as seen from the underside thereof.

Referring to FIGS. 6 and 7, the blade body 24 is formed from a blank 25 of deformable material and is shaped to fit in a carrier, such as carrier 22. As shown, it is of a generally oval configuration with a uniform array of teeth 73 formed thereon.

The skin care device 20 of the present invention is so designed as to lend itself to a highly efficient manufacturing process in which the blade body 24, and the carrier 22 therefor, may be formed into a fully integrated unit. More specifically, the blade body 24 is ideally suited to be formed by a photochemical etching process and, in particular, a single sided etching process such as that disclosed and taught in Sturtevant U.S. Pat. No. 5,100,506, which process provides an exceptionally uniform sharp edge. It will be understood, however, that other methods of manufacture, consistent with the objectives to be achieved, are within the contemplation of the invention.

A preferred manufacturing process involves the initial etching of a flat blank of material to form the outer profile of the blade body and the teeth within that profile. Referring to FIGS. 6 and 7, the periphery of the blade body 24 is formed with a series of tabs 53 which circumscribe the blade body. The blank so formed is then placed in a die, or mold, where the tabs 53 are bent, referring to FIG. 6, upon compression of the blank in the die and a moldable material, such as plastic, is injected, or otherwise introduced into the die.

In a preferred method of manufacture, the moldable material forms the carrier within the die about the blade body, simultaneously encapsulating the tabs in the moldable material, thereby securing the blade in the carrier. It is recognized that other manufacturing procedures may be used to create the device of the present invention without departure from the essential features thereof. The carrier comprises a continuous side wall completely circumscribing the blade body and projecting below the plane of the blank, fixedly and permanently holding the blade body in the carrier about a peripheral region of the blade body, with the carrier not protruding above the plane of the blank.

While the palm held carrier 20 is very useable for many people, there are instances, and locations, of unsightly skin buildup where such a carrier is less than helpful. For those folks, the invention contemplates the use of other carriers, e.g., the hand held carrier 60, illustrated in FIGS. 4 and 5.

An ergonomically pleasant carrier 60 is formed with a head section 62, which is formed, or otherwise provided, at the end of a handle section 64. The head section 62 is oval in configuration and adapted to receive a blade body, e.g., the blade body 24. The handle section 64 is gently curved away from the head section to the tip 66, where an aperture is formed to permit storage of the device on a hook, or the like, as desired. The handle provides to the user an ability to reach to otherwise less accessible areas of the body in order to remove unwanted skin.

The present invention contemplates a blade body which is bi_directional in operation. Referring to FIGS. 6 and 7, such a blade body 71 is illustrated. The blade body 71 is conveniently formed from a blank having an oval shape, although clearly, if the carrier is adapted to receive another shape, it would be readily accomplished. Several rows of bi-directional teeth 73 are formed in transverse relation to the longitudinal axis of the blade, perhaps best illustrated in FIG. 6.

Considering now FIGS. 8 through 11, several amplified views of a bi-directional tooth of the present invention are illustrated in some detail. Each tooth 73 is provided with oppositely extending elements defining oppositely extending, preferably elements of substantially equal length, each of said elements termination in discreet opposed cutting edges 75 and 76. Each of the edges, as illustrated, coplanar and raised by a predetermined small amount from the plane of the blank 78, from which the cutting edges are formed in order that the cutting edges are exposed to the area of skin to be treated. The height, "H" of the cutting edges 75, 76 relative to the plane of the blank 78 is carefully controlled to a dimension of no more than 0.025" in order to assure the user that only a very minimal amount of excess skin would be removed in a given stroke of the device.

Figure 8:
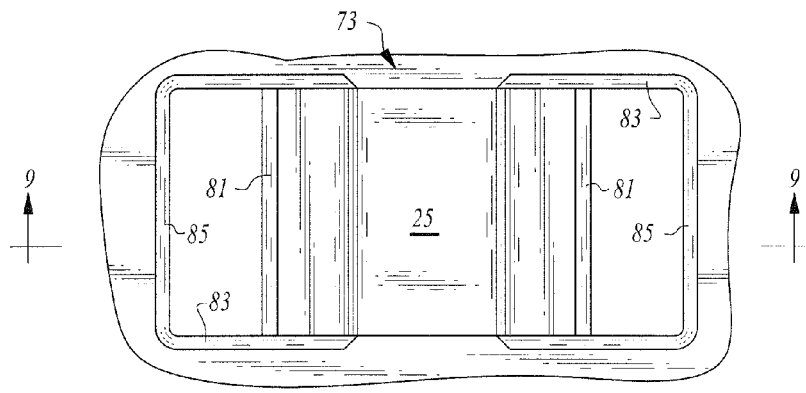
FIG. 8 is an enlarged, fragmented top plan view of a portion of the cutter blade of FIG. 6, illustrating the raised cutting surfaces of that cutter blade.

As may be viewed in FIG. 8, the raised edges define, with the blank 25 from which the blade is formed, a channel indicated by arrows 87. The channel provides for a controlled tunnel-like chute, beneath the cutting edge, through which material, in the nature of dead skin, is quickly funneled away from the area to be treated and through the openings 83.

As previously alluded to, in forming the finished blade body covered by the present invention, a photo chemical etching process, such as that disclosed in the aforementioned Sturtevant et al. '506 patent, is ideally suited to the manufacture of the blade body. By using such an etching process, each opening 83 is first formed in the blank 78, and the profile of the blade is thus defined.

The resultant opening 83 is defined by peripheral edges. Opposed ones of the edges, 75, 76, in the present scenario, resulting from the formation of that opening, are upset, by pressing them in a die, to move the edges by a height "H" above the plane of the blank 78.

Furthermore, upsetting the edges 75 and 76 in a die provides a softer transition between an adjacent edge and the raised or upset edge. As a result, there is less likelihood that debris of any kind would hang up or accumulate in that area, thereby enhancing the integrity of the device.

In summary this novel device is provided for the gentle, yet safe, removal, by means of a to and fro planing action, of unwanted skin buildup in the nature of callouses and corns. The invention contemplates two convenient carrier styles which receive the blade body, providing the consumer with choices to fit his or her particular needs.

It will be apparent to those skilled in the art that minor variations in one or more of the elements of the invention are possible without departure from the invention, wherein it is claimed:

The invention claimed is:

1. A device for the gentle removal of excess, or unwanted buildup, of skin on parts of the human body comprising, in combination:
    a carrier;
    a planar blade body secured in said carrier, said blade body being formed from a deformable blank and including a plurality of discrete cutting teeth, said teeth protruding above the plane of said blank by a predetermined distance; each said tooth including oppositely extending elements and having at least two uniform and discrete opposed cutting edges;
    said edges being substantially coplanar;
    said carrier comprising a continuous side wall completely circumscribing said blade body and projecting below the plane of the blank, fixedly and permanently holding the blade body in said carrier about a peripheral region of said blade body, with said carrier not protruding above the plane of the blank, such that a to and fro movement of said carrier when said teeth are in contact with skin to be removed results in removal of controlled amounts of excess skin with each such movement,
    wherein said carrier side wall comprises an upstanding shell having two opposed ends, said blade body being fitted into one of said ends;
    wherein a cap is provided for said device, said cap being fitted over said one end to protect said blade body when said device is not in use; and
    wherein the surface of said cap is fitted with an abrasive material.

2. The device of claim 1, wherein each tooth comprises a pair of opposed cutting edges.

3. The device of claim 2, wherein an opening is formed in said blade body; opposed edges of said blank are deformed upwardly in a smooth transition from the surface of said blade body, said upturned edges defining cutting edges.

4. The device of claim 1, wherein said cutting edges are raised less than 0.025" above said deformable blade body.

5. The device of claim 4, wherein said blade body is formed by a single sided photochemical etching process.

6. The device of claim 1, wherein said blade body is formed by a single sided photochemical etching process.

7. The device of claim 1, wherein each tooth comprises an array of cutting elements, said cutting elements having opposed cutting edges on each.

8. The device of claim 1, wherein an opening is formed beneath each tooth, said teeth and said blade body together defining a channel for the removal of particulate matter removed by said cutting edges from the area of skin to be treated.

9. The device of claim 1, wherein said carrier further comprises a handle attached to said wall.

10. The device of claim 1, wherein
    said deformable blank is flat and
    an opening is formed beneath each said cutting edge, said tooth and said blade body about said opening together defining channels, each said channel being positioned to guide particulate material removed from the area to be treated through said opening and away from said cutting edges;
    the distance between said cutting edge and said blade body about said opening being no more than 0.025" so as to remove a minimal amount of excess skin in a given stroke.

11. The device of claim 10, wherein said blade body is formed by a single sided photochemical etching process.

12. A device for the gentle removal of excess, or unwanted buildup, of skin on parts of the human body comprising, in combination:
    a carrier;
    a planar blade body secured in said carrier;
    said blade body being formed from a deformable blank and including a plurality of discrete cutting teeth, said teeth protruding above the plane of said blank by a predetermined distance; each said tooth having at least two uniform and discrete opposed cutting edges;
    said carrier comprising a continuous side wall completely circumscribing said blade body and projecting below the plane of the blank, fixedly and permanently holding the blade body in said carrier, with said carrier not protruding above the plane of the blank, such that a to and fro movement of said carrier when said teeth are in contact with skin to be removed results in removal of controlled amounts of excess skin with each such movement; and
    wherein a series of tabs are provided about a peripheral region of said blade body, said tabs circumscribing said blade body, said tabs being secured in said carrier to affix said blade body in said carrier, wherein said carrier side wall comprises an upstanding shell having two opposed ends, said blade body being fitted into one of said ends;

wherein a cap is provided for said device, said cap being fitted over said one end to protect said blade body when said device is not in use; and wherein the surface of said cap is fitted with an abrasive material.

13. The device of claim 12, wherein said tabs are formed integrally on the periphery of said blade body.

14. A device for the gentle removal of excess, or unwanted buildup, of skin on parts of the human body comprising, in combination:

a carrier;

a planar blade body secured in said carrier, said blade body being formed from a deformable blank and including a plurality of discrete cutting teeth, said teeth protruding above the plane of said blank by a predetermined distance; each said tooth including oppositely extending elements and having at least two uniform and discrete opposed cutting edges;

said edges being substantially coplanar;

said carrier comprising a continuous side wall completely circumscribing said blade body and projecting below the plane of the blank, fixedly and permanently holding the blade body in said carrier about a peripheral region of said blade body, with said carrier not protruding above the plane of the blank, such that a to and fro movement of said carrier when said teeth are in contact with skin to be removed results in removal of controlled amounts of excess skin with each such movement, wherein said carrier comprises an upstanding oval shell having first and second ridges and a center section there between, said center section having a concave side wall, said blade body being fitted into one of said ridges;

wherein a cap is provided for said device, said cap being fitted over said one ridge to protect said blade body when said device is not in use; and wherein the surface of said cap is fitted with an abrasive material.

15. A device for the gentle removal of excess, or unwanted buildup, of skin on parts of the human body comprising, in combination:

a carrier;

a planar blade body defining a generally flat plane and being secured in said carrier;

said blade body being formed from a deformable generally planar blank and including a plurality of discrete cutting teeth, at least a portion of said teeth protruding above the plane of said blank by a predetermined distance;

each said tooth having at least two uniform and discrete opposed cutting edges; said edges being substantially coplanar; said edges being bidirectional in that the edges are generally directly opposite each other and are facing in generally opposite directions;

said carrier comprising a continuous side wall completely circumscribing said blade body and projecting below the plane of the blank, fixedly and permanently holding the same in said carrier about a peripheral region of said blade body, with said carrier not protruding above the plane of the blank, such that a to and fro movement of said carrier when said teeth are in contact with skin to be removed results in removal of controlled amounts of excess skin with each such movement; and said carrier being graspable in the palm of a user's hand such that the blade body faces away from the palm and is movable against and across an area of the user's skin to be treated while being thus grasped, wherein said carrier side wall comprises an upstanding shell having two opposed ends, said blade body being fitted into one of said ends;

wherein a cap is provided for said device, said cap being fitted over said one end to protect said blade body when said device is not in use; and wherein the surface of said cap is fitted with an abrasive material.

16. A device for the gentle removal of excess, or unwanted buildup, of skin on parts of the human body comprising, in combination:

a carrier;

a planar blade body secured in said carrier, said blade body being formed from a deformable blank and including a plurality of discrete cutting teeth, said teeth protruding above the plane of said blank by a predetermined distance;

said carrier comprising a continuous side wall completely circumscribing said blade body and projecting below the plane of the blank, fixedly and permanently holding the blade body in said carrier about a peripheral region of said blade body, with said carrier not protruding above the plane of the blank, such that a to and fro movement of said carrier when said teeth are in contact with skin to be removed results in removal of controlled amounts of excess skin with each such movement, wherein said carrier side wall comprises an upstanding shell having two opposed ends, said blade body being fitted into one of said ends;

wherein a cap is provided for said device, said cap being fitted over said one end to protect said blade body when said device is not in use; and wherein the surface of said cap is fitted with an abrasive material.

\* \* \* \* \*